(12) United States Patent
Fetsko et al.

(10) Patent No.: US 7,820,866 B2
(45) Date of Patent: Oct. 26, 2010

(54) PROCESS FOR THE MANUFACTURE OF POLYPHENOLS

(75) Inventors: Stephen W. Fetsko, Hingham, MA (US); Steven D. Evitt, Somerville, MA (US)

(73) Assignee: Badger Licensing LLC, Cambridge, MA (US)

( * ) Notice: Subject to any disclaimer, the term of this patent is extended or adjusted under 35 U.S.C. 154(b) by 121 days.

(21) Appl. No.: 12/299,153

(22) PCT Filed: May 4, 2006

(86) PCT No.: PCT/US2006/017360

§ 371 (c)(1), (2), (4) Date: Dec. 30, 2008

(87) PCT Pub. No.: WO2007/130040

PCT Pub. Date: Nov. 15, 2007

(65) Prior Publication Data

US 2009/0137848 A1    May 28, 2009

(51) Int. Cl.
*C07C 37/20*    (2006.01)

(52) U.S. Cl. ...................................... 568/728; 568/727
(58) Field of Classification Search .................. None
See application file for complete search history.

(56) References Cited

U.S. PATENT DOCUMENTS

| | | | |
|---|---|---|---|
| 2,468,982 | A | 5/1949 | Jansen |
| 2,602,821 | A | 7/1952 | Luten, Jr. et al. |
| 2,730,552 | A | 1/1956 | Williamson |
| 6,465,697 | B1 | 10/2002 | Palmer et al. |

FOREIGN PATENT DOCUMENTS

| | | |
|---|---|---|
| EP | 0112615 | 7/1984 |
| JP | 63023830 | 2/1988 |
| WO | 02/059069 | 8/2002 |
| WO | 02083611 | 10/2002 |

*Primary Examiner*—Brian J Davis
(74) *Attorney, Agent, or Firm*—Roberts, Mlotkowski, Safran & Cole, P.C.

(57) ABSTRACT

An improved process for the manufacture of a polyphenol compound such as bisphenol-A by introducing into a reaction zone a phenolic compound reactant, a carbonyl compound reactant, and a catalyst promoter comprising bismethylthiopropane added to the reaction system in certain specific locations, and reacting the ingredients within the reaction zone in the presence of an acid catalyst.

40 Claims, 1 Drawing Sheet

PROCESS FOR THE MANUFACTURE OF POLYPHENOLS

FIELD OF THE INVENTION

The present invention relates to an improved process for the manufacture of polyphenols, and more specifically to an improved, safe process for such manufacture, whereby the addition of an effective catalyst promoter to the process reaction system is limited to certain specific locations.

BACKGROUND OF THE INVENTION

The polyphenol compound 2,2-bis(4-hydroxyphenyl)propane, also called para, para-diphenylolpropane or bisphenol-A ("BPA"), is generally prepared by reacting phenol and acetone in the presence of an acidic condensation catalyst along with a catalyst promoter or cocatalyst to increase the reaction rate and selectivity of the condensation catalyst. U.S. Pat. No. 2,468,982, incorporated herein by reference, disclosed the use of mercapto-substituted aliphatic carboxylic acids as catalyst promoters to increase the condensation reaction rate between phenols and ketones. It was later disclosed in U.S. Pat. No. 2,730,552, incorporated herein by reference, that contact time in the acid-catalyzed reaction between phenol and ketones was improved by the use of methyl mercaptans as promoter. Not only was the contact time reduced, but the use of gaseous methyl mercaptan in the reaction zone permitted running the reaction with only minimal amounts of catalyst promoter without the formation of substantial amounts of by-product formation or bisphenol-A product disintegration. Further, methyl mercaptan could be used as a catalyst promoter in a continuous process. Methyl mercaptan was also distinguished in that its high volatility allowed it to be easily separated from the reactor effluent containing bisphenol-A product and avoided the presence of sulfur contaminants in the final product. Since then, the use of gaseous free methyl mercaptan has been the catalyst promoter of choice in acid-catalyzed phenol-acetone reactions.

However, methyl mercaptan is difficult to handle because it is gaseous at room temperature and atmospheric pressure. This makes the shipping of methyl mercaptan inefficient because it must first be pressurized to a liquid state to economically transport sufficient amounts required for the manufacture of bisphenol-A to a plant located some distance from the site producing methyl mercaptan. Moreover, since methyl mercaptan is a hazardous compound, in some cases shipping this material to certain locations is restricted, resulting in limited availability in these areas. As a result, some bisphenol-A plants must now either produce methyl mercaptan on site, or switch to an alternative catalyst promoter which does not have the volatility of methyl mercaptan.

U.S. Pat. No. 6,465,697, incorporated herein by reference, discloses dithioketals, particularly bismethylthiopropane ("BMTP"), as a promoter for the acid-catalyzed condensation reaction between phenols and carbonyl compounds at substantially the same rate and with substantially the same selectivity towards bisphenol-A as methyl mercaptan and without the formation of any by-product sulfur species at levels greater than with the use of methyl mercaptan. The BMTP promoter is not as volatile as methyl mercaptan, is liquid at room temperature and atmospheric pressure and stable during transportation, thereby rendering it easily and economically transportable. BMTP catalyst promoter proved to have high activity and high selectivity. The amount of sulfur byproduct species produced using this catalyst promoter is acceptably low.

SUMMARY OF THE INVENTION

We have now discovered an improved method for using BMTP as catalyst promoter in the condensation process for manufacture of polyphenols, such as BPA.

This method involves a condensation process for the manufacture of a polyphenol compound comprising introducing into a reaction zone ingredients comprising a phenolic compound reactant, a carbonyl compound reactant, and bismethylthiopropane catalyst promoter, said promoter added to the reaction at certain specific locations of the reaction system, and condensing the phenolic compound and the carbonyl compound in the presence of an acid catalyst. The location of BMTP promoter introduction into the reaction system is critical for the most efficient and safe reactor operation.

More specifically, there is provided a method for the manufacture of a polyphenol compound in a reaction system comprising adding together a phenolic compound, a carbonyl compound, bismethylthiopropane catalyst promoter, said promoter added to the reaction system at certain specific locations of the reaction system, hydrolyzing the bismethylthiopropane catalyst promoter to its dissociation products, and condensing the phenolic compound and the carbonyl compound in the presence of an acid catalyst and said dissociation products.

Still more specifically, there is provided a method for the manufacture of BPA in a reaction system comprising adding together a phenol, acetone, bismethylthiopropane catalyst promoter, said promoter added to the reaction system at certain specific locations of the reaction system, hydrolyzing the bismethylthiopropane catalyst promoter to its dissociation products including methyl mercaptan and acetone, and condensing the phenol and acetone in the presence of an acid catalyst and said dissociation products.

DETAILED DESCRIPTION OF THE INVENTION

Figure 1:
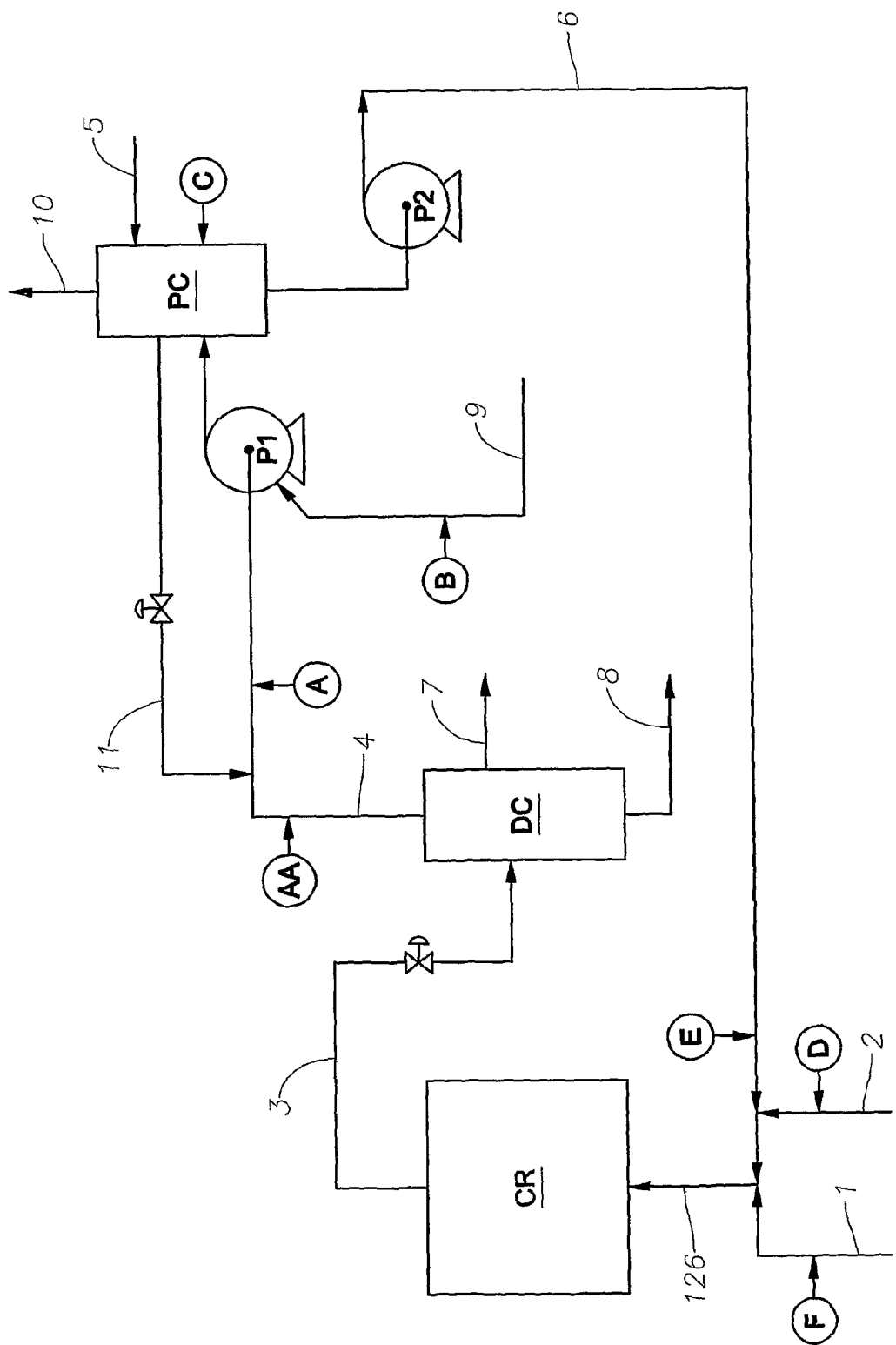
FIG. 1 is a flow diagram of a reaction system within a process for production of polyphenols, e.g. BPA.

The polyphenols manufactured by the process of the present invention include those prepared by the reaction of a carbonyl compound reactant with a phenolic compound reactant. Examples of carbonyl compounds are those compounds represented by the following formula:

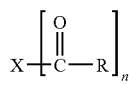

wherein R represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated; n is greater than 0, preferably from 1 to 3, more preferably from 1-2, and most preferably is 1; and when n is greater than 1, X represents a bond, or a multivalent linking group having from 1 to 14 carbon atoms, preferably from 1 to 6 carbon atoms, more preferably from 1 to 4 carbon atoms; and when n is 1, X represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated, provided that X and R are not both hydrogen.

Suitable carbonyl compounds for use herein include aldehydes and ketones. These compounds generally contain from three to fourteen carbon atoms, and are preferably aliphatic ketones. Examples of suitable carbonyl compounds include ketones such as acetone, methyl ethyl ketone, diethyl ketone, dibutyl ketone, isobutyl methyl ketone, acetophenone, methyl and amyl ketone, cyclohexanone, 3,3,5-trimethylcyclohexanone, cyclopentanone, 1,3-dichloroacetone and the like. The most preferred is acetone.

The carbonyl compounds are reacted with phenolic compounds. Phenolic compounds are aromatic compounds containing an aromatic nucleus to which is directly bonded at least one hydroxyl group. Phenolic compounds suitable for use herein include phenol and the homologues and substitution products of phenol containing at least one replaceable hydrogen atom directly bonded to the aromatic phenol nucleus. Such groups substituting for the hydrogen atom and directly bonded to the aromatic nucleus include the halogen radicals such as chloride and bromide, and the hydrocarbon radicals such as alkyl, cycloalkyl, aryl, alkaryl and aralkyl groups. Suitable phenolic compounds include phenol, the cresols, the xylenols, carvacrol, cumenol, 2-methyl-6-ethyl phenol, 2,4-dimethyl-3-ethylphenol, o-chlorophenol, m-chlorophenol, o-t-butylphenol, 2,5-xylenol, 2,5-di-t-butylphenol, o-phenylphenol, 4-ethylphenol, 2-ethyl-4-methylphenol, 2,3,6-trimethylphenol, 2-methyl-4-tertbutylphenol, 2-tertbutyl-4methylphenol, 2,3,5,6-tetramethylphenols, 2,6-dimethylphenol, 2,6-ditertbutylphenol, 3,5-dimethylphenol, 2-methyl-3,5-diethylphenol, o-phenylphenol, p-phenylphenol, naphthols, phenanthrol, and the like. Most preferred are compositions comprising phenol. Mixtures of any of the above may be used.

The above is not meant to limit the invention but to illustrate representative examples of carbonyl compounds and phenolic compounds which are known in the art to make desirable polyphenol and for which those of skill in the art can substitute other similar reactants.

In the preparation of the polyphenols, an excess of the phenolic compound reactant over the carbonyl compound reactant is usually desirable. Generally at least about 2, preferably from about 4 to about 25, moles of phenolic compound per mole of carbonyl compound is desirable for high conversion of the carbonyl compound. Solvents or diluents are not necessary in the process of the present invention for the manufacture of the polyphenol except at low temperature.

The polyphenol compounds obtained by the condensation reaction of a phenolic compound and a carbonyl compound in the present process are compounds wherein the nuclei of at least two phenolic radicals are directly attached by carbon to carbon linkages to the same single carbon atom in the alkyl group. An illustrative non-limiting example of a polyphenol compound is represented by the formula:

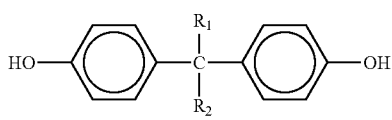

wherein $R_1$ and $R_2$ each independently represent a monovalent organic radical. Examples of such radicals include hydrocarbon radicals such as aliphatic, cycloaliphatic, aromatic, or heterocyclic radical, more specifically hydrocarbon radicals such as alkyl, cycloalkyl, aryl, aralkyl, alkaryl, whether saturated or unsaturated. Preferably, $R_1$ and $R_2$ each independently represent an alkyl radical having from 1 to 2 carbon atoms. Most preferably, the polyphenol compound comprises bis (4-hydroxyphenyl) propane, i.e. bisphenol-A ("BPA").

Polyphenol compounds are made by the acid-catalyzed reaction between a phenolic compound and a carbonyl compound. The rate and selectivity of the reaction are promoted by introducing into the reaction zone a catalyst promoter, such as in the present invention BMTP.

The BMTP catalyst promoter is 2,2-bis (methylthio) propane, or herein simply bismethylthiopropane ("BMTP"), represented by the following structure:

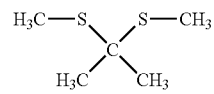

This catalyst promoter compound is chosen for the present process because it is a type which, upon dissociation in the reaction zone, forms the same or chemically similar kind of carbonyl compound as the feed carbonyl compound chosen to make the polyphenol. In one embodiment, the feed carbonyl compound is acetone and the catalyst promoter composition comprises BMTP, which in the presence of the acid catalyst and water dissociates into acetone and methyl mercaptan catalyst promoter.

BMTP catalyst promoter has essentially the same first order rate for converting the carbonyl compound as its dissociation product methyl mercaptan. It also has essentially the same selectivity toward formation of the polyphenol product as its dissociation product methyl mercaptan.

To the reaction vessel is added the phenolic compound, the carbonyl compound, catalyst promoter, and optionally a solvent and water. The acid catalyst, depending upon the type used, may be charged to the reaction vessel or may be loaded into the reaction vessel prior to charging the liquid feeds. The addition sequence of reactants, catalyst promoter, catalyst and optional solvent and water to a reaction vessel is not limited in the prior art. In the present improved process, however, the manner of introducing the catalyst promoter to the reaction mixture is limited to being added only at certain locations of the reaction system. The prior art teaches that catalyst promoter compositions can be added anytime and anywhere in the reaction system, such as to a reaction mixture containing all reactants and catalyst and optional solvent, or to a reaction mixture containing only some of these ingredients, or to any feed stream containing any one of these individual ingredients or a mixture of these ingredients. Thus, introduction of the catalyst promoter in the prior art to the reaction mixture includes its addition to any one or a mixture of any one or all of the ingredients used to make the polyphenol.

The process of the present invention requires introducing the BMTP promoter at certain specific locations of the reaction system, in contrast to simply adding a mercaptan, such as methyl mercaptan, to the reaction mixture and in contrast to contacting a phenolic compound and a carbonyl compound with a dithioketal compound formed in situ by, for example, the reaction of acetone with methyl mercaptan.

The reversible formation of bismethylthiopropane (BMTP) from methyl mercaptan and acetone in the presence of an acid catalyst has been reported in *Org. Chem. of Bivalent Sulfur: Volume III*, E. Emmet Reid, 1960. The reaction proceeds according to the following equilibrium, where BMTP is referred to as "DMA" (dimethanethioketal of acetone):

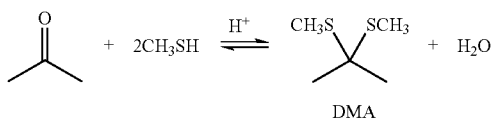

DMA

U.S. Pat. No. 6,465,697, incorporated herein by reference, teaches adding BMTP to the reaction mixture instead of adding methyl mercaptan to the reaction mixture. It was found that BMTP rapidly hydrolyzes and equilibrates to the formation of methyl mercaptan in situ without any induction time. The process of the invention forms methyl mercaptan in situ, thus avoiding the need to isolate, ship and handle methyl mercaptan. Due to the lower volatility and better stability of BMTP at room temperature and atmospheric conditions, it is more advantageous to isolate, ship and handle BMTP and introduce it to the reaction system.

The BMTP catalyst promoter composition is added to the reaction mixture or to any one of the reactants in the liquid phase or in the gaseous phase at any place in the reaction system in U.S. Pat. No. 6,465,697.

Embodiments of the present invention are illustrated by reference to FIG. 1. In FIG. 1, liquid feedstock comprising phenolic compound, for example phenol, and optionally a solvent and/or water are provided via stream 1 for addition into condensation reactor CR. If the feed in stream 1 comprises mother liquor recycled from a down stream BPA purification step, it may comprise predominantly phenol, some acetone, water, solvent, BPA and byproducts. Optionally, water may be added to stream 1 to adjust the water concentration of the stream prior to entering the condensation reactor CR. Stream 1 is referred to herein as the phenolic compound/mother liquor stream. Liquid feedstock carbonyl compound, for example acetone, is provided via stream 2, herein the carbonyl compound stream. Stream 6 is referred to herein as the promoter absorber column bottoms stream. Streams 1, 2 and 6 are combined to create the condensation reactor feed stream 126 for addition to condensation reactor CR. The combined feedstock phenolic compound to carbonyl compound molar ratio as added to condensation reactor CR is at least about 2, preferably from about 4 to about 25. Liquid condensation reactor effluent stream 3, comprising polyphenol, for example BPA, and unreacted phenolic and carbonyl compounds, for example phenol and acetone, is removed from condensation reactor CR and delivered to dehydration column DC. From the dehydration column DC are drawn dehydration column overhead stream 4 as vapor under vacuum, liquid dehydration column side draw stream 7 under vacuum comprising predominantly water, and liquid dehydration column bottoms stream 8 under vacuum comprising predominantly polyphenol product, for example BPA, and unreacted phenolic compound, for example phenol. Dehydration column overhead stream 4 is pumped by pump P1 into promoter absorber column PC along with additional liquid phenolic compound, for example phenol, via first phenolic compound stream 5. Liquid bottoms from promoter absorber column PC comprising predominantly phenolic compound, for example phenol, is withdrawn from column PC using pump P2 as promoter absorber column bottoms stream 6 and recycled to form part of condensation reactor feed stream 126. Additional liquid phenolic compound, for example phenol, is supplied via second phenolic compound stream 9 to the pump P1 liquid ring fluid inlet port which creates the vacuum for dehydration column overhead stream 4 and the dehydration column DC. A vent stream 10 vents lights overhead from promoter absorber column PC. A vapor recirculation stream 11 is drawn from promoter absorber column PC and delivered to dehydration column overhead stream 4 upstream of pump P1 for the purpose of pressure control.

Condensation reactor CR may be a single reactor vessel, or two or more reactor vessels in parallel or series containing any suitable heterogeneous catalyst to effect the condensation of carbonyl and phenolic compounds to synthesize polyphenol, including but not limited to cationic ion exchange resins, may be upflow or downflow, may contain suitable hardware to distribute flow, support and contain catalyst, and the catalyst bed may be packed, expanded, partially fluidized or fully fluidized.

Dehydration column DC may be a distillation column containing suitable internals such as valve or sieve trays, structured or dumped packing, and distribution hardware or chimney trays and collection trays, with generally countercurrent flow between up flowing vapor and down flowing liquid. It may contain an internal stab-in condenser design well known to those knowledgeable in the art.

Promoter absorber column PC may be a distillation/adsorption column containing suitable internals such as valve or sieve trays, structured or dumped packing, and distribution hardware or collection trays, with generally countercurrent flow between up flowing vapor and down flowing liquid.

The BMTP catalyst promoter composition is liquid at room temperature and at atmospheric pressure (one atmosphere) which is convenient for safety and ease of shipping and handling. It is stable for transportation, is not readily decomposed at moderate temperatures in the absence of acid catalysts and water, and its thermal decomposition half life at 120° C. is greater than 40 hours.

The BMTP catalyst promoter composition is introduced into the reaction system neat or in solution. As a solution, it may be mixed with a portion or with the entire carbonyl compound used to make the polyphenol. The BMTP catalyst promoter composition may be added according to the present invention in at least one of points A, AA, B, C, D, E or F of FIG. 1, in that order of preference. Point A may be described as a point in the dehydration column overhead stream 4 downstream of the dehydration column DC, downstream of the point at which the vapor recirculation stream 11 enters stream 4, and upstream of the pump P1 creating a vacuum in said dehydration column overhead stream 4. Point AA may be described as a point in the dehydration column overhead stream 4 downstream of the dehydration column DC, upstream of the point at which the vapor recirculation stream 11 enters stream 4, and upstream of the pump P1 creating a vacuum in said dehydration column overhead stream 4. Point B may be described as a point in the second phenolic compound stream 9 to the pump P1 liquid ring fluid inlet port. Point C may be described as a point entering promoter absorber column PC, preferably above the liquid level in the bottom section of the promoter absorber column PC, and most preferably above the liquid level in the bottom section of the promoter absorber column PC and below the entry of the discharge stream from pump P1 into the promoter absorber column PC. Point D may be described as a point in the carbonyl compound stream 2 upstream of the junction with promoter absorber column bottoms stream 6. Point E may be described as a point in the promoter absorber column bottoms stream 6 upstream of the junction with either phenolic compound/mother liquor stream 1 or carbonyl compound stream 2. Point F may be described as a point in the phenolic compound/mother liquor stream 1 upstream of the junction with the condensation reactor feed stream 126. The BMTP catalyst promoter composition may be added incrementally or continuously over the course of the reaction, or all of the required catalyst promoter may be added to these points of the reaction system. Backflow from the BMTP addition point to the BMTP storage system is undesirable because the presence of acid (including acids even as weak as phenol) and water can lead to decomposition of BMTP to methyl mercaptan and acetone, the formation of which could create a potential hazard. All of the BMTP addition locations in this system except point D contain both phenol and water of sufficiently high concentrations to cause BMTP decomposition.

Point A is most preferred because the addition location is under vacuum, thereby creating minimal risk that the destination inventory could backflow into the BMTP storage system. Point AA is preferred during normal operation of the reaction system since it is under vacuum with minimal risk that the destination inventory could backflow into the BMTP storage system. Point B is preferred because the addition location is under vacuum as stream 9 enters the liquid ring inlet port of pump P1. Point B should be located as close as practical to the liquid ring inlet port of pump P1. Point C is preferred because the pressure of the promoter absorber column PC is significantly lower than the combined condensate reactor feed stream 126 or individual streams 1, 2 or 6. The preferred location of point C is above the liquid level in the promoter absorber column PC and therefore less prone to backflow of phenol. Point D is preferred because the carbonyl compound stream 2 is free of any phenolic or other acidic component and typically has a low water concentration. In particular, when acetone is the carbonyl compound, backflow of acetone into the BMTP storage system would tend to minimize extent of any decomposition of BMTP because of excess acetone concentration. Points E and F are less preferred because of higher potential for backflow of phenol and water to the BMTP storage system due to the higher pressures of streams 1 and 6 in combination with presence of phenolic compound and water in these streams.

The rate of adding BMTP catalyst promoter composition to the reaction system is not limited. The manner for introducing the catalyst promoter composition is also not limited. It may be metered and injected at the point AA or A through F, preferably at points AA or A through D, most preferably at point A, by suitable means designed to supply the catalyst promoter safely and without backflow into the BMTP supply system.

Preferably, the BMTP catalyst promoter composition is introduced as a pure composition into the reaction mixture, meaning that outside of those ingredients used to make the polyphenol which are mixed with the catalyst promoter, the catalyst promoter composition comprises at least 90 wt. % BMTP, more preferably at least 95 wt. % BMTP, most preferably at least 98 wt. % BMTP. Whether or not a pure composition of BMTP catalyst promoter is used, the amount of impurities present in the catalyst promoter composition which are a reactive species with the phenolic compound, the carbonyl compound, or the catalyst, is preferably less than 2 wt. %, more preferably less than 1 wt. %, most preferably less than 0.2 wt. %. Higher compositions of BMTP are preferred because they lead to lower shipping costs for delivery of BMTP to the plant site.

The exact molar amount of the BMTP catalyst promoter composition as a fresh initial charge to the reaction system will depend upon the particular reaction conditions employed, the species of phenolic and carbonyl compounds selected, and the kind of catalyst used. Generally, however, the molar ratio of BMTP catalyst promoter compound to the carbonyl compound used as the fresh initial charge to the reaction zone in the process of the invention ranges from 0.005:1 up to 0.5:1, preferably from 0.05:1 to 0.25:1. In one embodiment, for the manufacture of bisphenol-A using phenol and acetone as reactants, the molar ratio of BMTP catalyst promoter compound to the carbonyl compound ranges from 0.025:1 to 0.25:1. The amount of BMTP catalyst promoter compound added to the reaction mixture is generally about half the molar ratio of a bisphenol-A manufacturing process equipped for the addition of methyl mercaptan since 1 mole of BMTP catalyst promoter yields two moles of the corresponding mono mercaptan catalyst promoter.

A method for initially charging BMTP into the reaction system is as follows:

Phenolic compound is inventoried into condensation reactor CR. Any phenolic compound from downstream flows through phenolic compound/mother liquor stream 1 and condensation reactor feed stream 126 into the condensation reactor CR and phenolic compound flows through first phenolic compound stream 5 into promoter absorber column PC. Phenolic compound flows from the condensation reactor CR to the dehydration column DC via condensation reactor effluent stream 3 and leaves the dehydration column DC from the dehydration column bottoms stream 8. Phenolic compound flow is also established from the bottom of the promoter absorber column PC into the promoter column bottoms stream 6 and condensation reactor feed stream 126. Carbonyl compound stream 2 contains no flow at this time. Demineralized or other similarly purified water is commissioned in the system to a level between about 0.5 wt % and 2 wt % of the reactor inventory (about 2.5-10.0 mol %). Water can be introduced into the promoter absorber column PC at either the top or the bottom, including into streams 6 or 126, or into the phenolic compound/mother liquor stream 1, or directly into the condensation reactor CR. BMTP is then introduced into the system until the methyl mercaptan level in the condensation reactor CR reaches from about 0.25 wt % to 2.0 wt %, preferably from about 0.5 wt % to 1.0 wt % (or 0.95 to 1.9 mol %). Water is in excess during this commissioning. For example, the BMTP is added at a rate to maintain a water/methyl mercaptan molar ratio in the condensation reactor during commissioning greater than about 1.0, preferably greater than about 2.0, until the methyl mercaptan in the condensation reactor reaches from about 0.25 wt % to about 2.0 wt %, preferably from about 0.5 wt % to about 1.0 wt %. The rate of BMTP injection is somewhat arbitrary, depending on design of piping and pumps, but it is conducted to insure that water is always in molar excess to methyl mercaptan. The total BMTP inventoried is such that it is equivalent to about 0.5 wt % (0.95 mol %) of the reactor inventory. The location of BMTP initial start up injection is at least one of points A, B, C or D. Point A is contained within the recirculation loop created by the vapor recirculation stream 11 from the promoter absorber column PC and the point at which it intersects the dehydration column overhead stream 4, upstream of pump P1. In other words, point A is in the dehydration column overhead stream 4 downstream of the dehydration column DC, downstream of the point at which the vapor recirculation stream 11 intersects the dehydration column overhead stream 4 and upstream of the pump P1 creating a vacuum in said dehydration column overhead stream 4. Point B is in the second phenolic compound stream 9 to the liquid ring inlet port of pump P1. Point C is into the promoter absorber column PC, preferably above the liquid level in the promoter absorber column PC. Point D is into stream 2 in which no carbonyl compound is flowing.

Once the reaction zone is charged with the fresh initial charge of the BMTP composition, for the following reason, the process advantageously requires only small amounts of BMTP as a fresh make-up charge to continue producing the desired yield. The feed stream(s) comprised of the phenolic compound, the carbonyl compound, and the catalyst promoter is contacted with an acid catalyst for a period of time sufficient to effect formation of the polyphenol product. In the reaction zone containing the phenolic compound, the carbonyl compound, the acid catalyst, and the catalyst promoter, the BMTP catalyst promoter rapidly hydrolyzes to its dissociation products, one of which is methyl mercaptan catalyst promoter, a compound having a thiol group covalently bonded to a carbon atom. Once the desired yield of polyphenol is attained by the condensation reaction between the phenolic compound and the carbonyl compound, the resulting crude reaction mixture effluent stream containing the polyphenol product is fed to a separation zone to separate the crude polyphenol compound into a crude polyphenol stream from at least a portion of other compounds such as unreacted carbonyl compounds, unreacted phenolic compounds, the dissociation products of the catalyst promoter which include methyl mercaptan catalyst promoter, and water byproduct from the condensation reaction. These compounds may be removed as an overhead or fractionally as draws by way of, for example, distillation or fractional distillation. The method of separation is not limited and can be any conventional method for separating such materials. Distillation is generally the simplest and most preferred method. However, other well known methods can be used independently or in combination with distillation to comprise this separation process.

Any fraction containing BMTP dissociation products, one of which is the mercaptan catalyst promoter, may be recycled back to the reaction zone or to any line or reactant feeding the reaction zone. This fraction may be recycled directly back to the reaction zone or may be optionally but preferably further processed to enrich the concentration of and recover the mercaptan catalyst promoter prior to recycling the mercaptan catalyst promoter back to the reaction zone. Depending upon the separation means used, all the overhead may be fed to a mercaptan recovery zone, or a fraction rich in the mercaptan may be fed to a recovery zone, or multiple fractions containing the mercaptan catalyst promoter may be fed to a recovery zone. The means for recovering the mercaptan catalyst promoter are not limited. For example, a stream containing the BMTP dissociation products including the mercaptan catalyst promoter compound may be fed to a catalyst promoter absorber column which comprises a column designed to efficiently contact the stream with phenol. In the catalyst promoter absorber column, the catalyst promoter dissociation products are absorbed from the rest of the tops products of the separator. The method of recovering the dissociation product catalyst promoter is not limited and can be any conventional technique, so long as the recovery zone functions to enrich the concentration of the mercaptan catalyst promoter relative to the concentration of the mercaptan catalyst promoter from the separation zone. The separated and recovered catalyst promoter dissociation products containing the mercaptan catalyst promoter compound are generally recycled to the reaction zone by way of a return line.

Substantially all of the mercaptan catalyst promoter can be recycled back to the reaction zone with only minimal losses. Once recycled to the reaction zone, the mercaptan catalyst promoter is just as effective to increase the activity of the acid catalyst and selectively convert the carbonyl compound to the polyphenol product as it was when formed from the dissociation of the BMTP catalyst promoter compound charged as a fresh initial charge to the reaction zone. Accordingly, after the fresh initial charge of BMTP to the reaction zone, only a fresh make-up charge of BMTP catalyst promoter composition is necessary to continue feeding the reaction system in order to make up for the amount of losses in the course of recovering and recycling the mercaptan catalyst promoter.

Thus, after the fresh initial charge of the BMTP catalyst promoter composition to the reaction zone, make up charges of the BMTP catalyst promoter compound may be added to the reaction system commensurate with the loss rate experienced by the process of separating and recycling the corresponding dissociation products of the catalyst promoter back to the reaction zone. Generally, more than 99% of the dissociation product catalyst promoter is recycled, meaning that less than 1 wt. % per hour of the BMTP needs to be charged as a makeup based on the total weight of mercaptan compounds in the reaction system. In one embodiment, for the manufacture of bisphenol-A using phenol and acetone as reactants, BMTP is charged to the reaction system at the chosen injection point(s) sufficient to maintain a methyl mercaptan level in the condensation reactor of from about 0.25 to about 2.0 wt %, preferably from 0.25 to about 1.5 wt %, more preferably from about 0.25 to about 1.0 wt %. Higher or lower amounts of the BMTP catalyst promoter may be introduced as needed.

Accordingly, an additional advantage to using BMTP catalyst promoter is that once charged as an fresh initial charge, the catalyst promoter does not have to flow through the process and be discarded or converted or neutralized. The dissociation products of the BMTP catalyst promoter are easily volatized, completely separated, and can be recycled back to the reaction zone and used as a catalyst promoter.

The polyphenol reaction conditions are any reaction conditions known to those skilled in the art for the manufacture of polyphenols. The specific reaction conditions will vary depending on the type of phenolic compound, solvent, carbonyl compound, and condensation catalyst selected. Generally, the phenolic compounds and the carbonyl compounds are reacted in a reaction vessel, whether in the batch or continuous mode, at a temperature ranging from about 20° C. to about 130° C., preferably from about 50° C. to about 130° C.

The pressure conditions are not particularly limited and the reaction may proceed at atmospheric, sub atmospheric or super atmospheric pressure. However, it is preferred to run the reaction either without any externally induced pressure, or at sufficient pressure to force the reaction mixture across a catalyst bed or to force the reaction mixture upstream in a vertical reactor, or to maintain the contents of the reaction vessel in a liquid state if the reaction is run at a temperature above the boiling point of any ingredient. The pressure and temperature should be set under conditions to retain the reactants in the liquid phase in the reaction zone. The temperature may exceed 130° C., but should not be so high as to degrade any of the ingredients in the reaction vessel, nor should it be so high as to degrade the reaction product or promote the synthesis to a substantial amount of unwanted by-products. The contact time ranges from about 15 minutes to about 4 hours, or until the desired yield of polyphenol is produced. The contact time of the polyphenol and carbonyl compound reactants over the acidic catalyst is equivalent to a weight hourly space velocity of from about 0.1 to about 10 $hr^{-1}$.

The reactants are introduced into the reaction zone under conditions to assure a molar excess of the phenolic compound over the carbonyl compound. Preferably, the phenolic compound is reacted in a substantial molar excess over the carbonyl compound. For example, the molar ratio of the phenolic compound to the carbonyl compound is preferably at least about 2:1, more preferably at least about 4:1, and up to about 25:1. Generally, the molar ratio of phenolic compound to carbonyl compound is maintained at a ratio of from about 4:1 to about 25:1.

Along with the BMTP catalyst promoter charged into the reaction system, a small amount of a hydrolyzing agent is required in the reaction zone in order assist the dissociation of the BMTP catalyst promoter into its dissociation products, e.g. free methyl mercaptan and acetone. A convenient hydrolysis agent is water, which may be introduced into any of the feed charges, directly into the reaction zone, or may be produced in situ by the condensation reaction between the carbonyl compound and the phenolic compound. A molar ratio of water to BMTP catalyst promoter ranging from about 1:1 to about 5:1 is sufficient to adequately hydrolyze the BMTP catalyst promoter. This quantity of water is produced in situ under typical reaction conditions. Thus, additional water does not need to be introduced into the reaction zone, although water may optionally be added if desired.

The reaction is normally conducted in an acidic medium at a pH ranging from 1 to 5. The condensation catalysts used in the process of the invention are any acidic catalysts known for condensing a phenolic compound with a carbonyl compound to make a polyphenol. The acid catalysts may be heterogeneous catalysts. These catalysts include the organo polysiloxanes containing sulfonic acid groups, solid perfluorinated polymer catalyst having pendant sulfonic groups which may be partially neutralized, acidic clays, or acidic ion exchange resins having a plurality of pendant sulfonic groups.

The acidic ion exchange resins are often mercaptan modified resins of the type conventionally known in the art which include any compound which will react with the acidic groups of the cation exchange resin to introduce a mercapto substituent into the resin. Suitable mercaptan modifying agents to be bound onto the acid sites of the exchange resin include alkyl mercapto amines such as propylaminopropyl mercaptan, bis-2-(mercaptoethyl)-amine, thiazolidine and the like.

The effectiveness of the acidic ion exchange resin in the condensation step of the process of the invention is to some extent influenced by its exchange capacities such that the greater the exchange capacity, the more desirable the resin. Preferably, the cation exchange capacity is at least about 0.5 and, more preferably, greater than about 4.0 meq/g dry weight. Also, those cation exchange resins having bound cationic exchange groups of the stronger exchange potential acids are preferred for use in the condensation step of the process of the present invention. Acidic cation exchange resins suitable (for optional modification with a mercapto modifying agent) for use in the condensation step of the process of the invention include sulfonated styrene-divinyl-benzene copolymers, sulfonated cross-lined styrene polymers, phenol-formaldehyde-sulfonic acid resins, benzene-formaldehyde-sulfonic acid resins, perfluorinated sulfonic acid resins and the like. These include resins under such trade names as Amberlites or Amberlysts (Rohm and Haas Co.), DOWEX (Dow Chemical Co.), Permutit QH (Permutit CO.), Chempro (Chemical Process Co.), catalysts from Purolite, Lewatit (LANXESS Deutschland GmbH), NAFIAN (DuPont) and the like. Strong acid sulfonated styrene-divinylbenzene copolymer resins are preferred.

Aromatic sulfonic acid resins are generally commercially available or can be obtained as sodium salts and converted to the acid form prior to use. Both macroreticular resins and microreticular resins are useful in the condensation process of the present invention. The choice of resin will of course depend on the starting materials, the reaction conditions and the effect of an individual resin under the conditions selected, which determination and selection is within the skill of the art.

The precise amount of acidic cation exchange resin to be used will vary to some degree depending on the specific resin, feed and conditions used for the process. By way of illustration, sufficient catalyst is loaded into the reaction zone to afford a contact time equivalent to a weight hourly space velocity of from about 0.1 to about 10 $hr^{-1}$. The feed stream comprised of the phenolic compound, the carbonyl compound, and the dithioketal catalyst promoter passes through the resin catalyst for a period of time sufficient to effect formation of the polyphenol depending on the feed rate, size of the resin bed, the particular resin and dithioketal catalyst promoter used and the like as can readily be determined by those of skill in the art.

Any suitable reactor may be used as the reaction zone. The reaction can occur in a single reactor, or in a plurality of reactors connected in series or in parallel. The reactor can be a back mixed or plug flow reactor, and the reaction can be conducted in a continuous or batch mode, and the reactor can be oriented to produce an up-flow or down-flow stream.

The invention is not limited to a particular method for recovering the polyphenol compound, and any method known to those of skill in the art is suitable. Generally, however, the crude reaction mixture effluent from the reaction zone is fed to a separator as mentioned above. The polyphenol product, polyphenol isomers, unreacted phenolic compound, and a small amount of various impurities are removed from the separator as a bottoms product. This bottoms product may be fed to a further separator. While crystallization is a common method of polyphenol separation but any method which can be used to separate polyphenol from the mother liquor can be used depending upon the desired degree of purity of the polyphenol product. Once separated, the mother liquor comprising phenol and polyphenol isomers may be returned to the reaction zone as reactant.

Polyphenol separated from mother liquor can then be sent to yet further separations and purifiers such as the polyphenol recovery process. This can be particularly important where very pure product is required as where BPA is produced for use in the subsequent production of polycarbonates. Generally, such further separations can be beneficially conducted using techniques such as recrystallization.

The present invention is illustrated by the following examples, which are not meant to be limiting within the spirit and scope of the invention as described herein.

EXAMPLE 1

U.S. Pat. No. 6,465,697, incorporated herein by reference, demonstrates that the rate, selectivity, and distribution of sulfur species for the acidic resin-catalyzed manufacture of BPA by the introduction of free BMTP as a catalyst promoter behaves substantially the same as with the use of methyl mercaptan (MeSH) added as a catalyst promoter.

Preparation of BMTP

To a three-neck round bottom flask equipped with a mechanical stirrer and a dry ice cold finger condenser was added 100 grams of acetone, 5 grams of CT122, a strongly acidic 2% cross linked sulfonated styrene divinylbenzene cationic gel exchange resin commercially available from Purolite, and 96 grams of methyl mercaptan. After stirring at ambient temperature for 3 hours and 40° C. for 1 hour, the liquid phase was decanted into 200 ml of methylene chloride and the combined washed mixture washed with 100 ml of water three times, dried over anhydrous magnesium sulfate, and concentrated by rotavap. The residue was fractionally distilled to yield 26 grams of bismethylthiopropane (BMTP) having a boiling point of 64-66° C. at 27 torr. Analysis of the sample by C13 NMR peaked at δ12.35 ("δ" means "Delta") corresponding to the presence of the $CH_3S$ group, and at δ29.63 corresponding to a $CH_3$ group, and at δ54.47, corresponding to the presence of a quaternary carbon atom.

Rate of Reaction for the Preparation of BPA

The rates of the acetone/phenol condensation catalyzed by the strongly acidic cationic exchange resin CT122, and promoted with MeSH and BMTP, respectively, were measured by in-situ IR. A mixture of phenol, water, and CT122 was preheated to 75° C. in an autoclave at autogeneous pressure, followed by injection with a solution of acetone and a promoter. The relative molar composition of the feed in the MeSH-promoted reaction was 100 moles of phenol, 8.1 moles of acetone, 2.8 moles of water, and 1.04 moles of MeSH. The relative molar composition of the feed in the BMTP-promoted reaction was the same except that MeSH was replaced with half the molar amount of BMTP. The weight ratio of phenol to CT122 was 100 to 3.17 in both reactions. The mixture was reacted over a period of about 3 hours, during which time the reaction rate was measured. The results of this experiment demonstrated that there was no induction period in the BMTP-promoted reaction and its first order rate for conversion of acetone was substantially identical to that of a MeSH-promoted reaction.

Selectivity Analysis

The selectivity of the catalyst promoter solutions to the formation of BPA were measured by HPLC. The following product distribution data show that replacing MeSH with BMTP has no effect on the selectivity of BPA formation. All numbers are in relative units.

| Promoter | % Acetone conversion | p, p-BPA | o, p-BPA | o, o-BPA | CDA* | CDB** | BPX*** | Unk. H**** |
|---|---|---|---|---|---|---|---|---|
| MeSH | 90 | 100 | 3.58 | 0.094 | 0.39 | 0.092 | 1.13 | 0.094 |
| BMTP | 90 | 100 | 3.52 | 0.091 | 0.4 | 0.1 | 1.2 | 0.11 |

*Cyclic Dimer A:

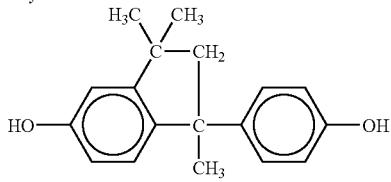

**Cyclic Dimer B:

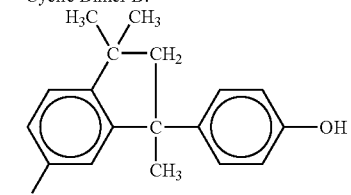

***Trisphenol:

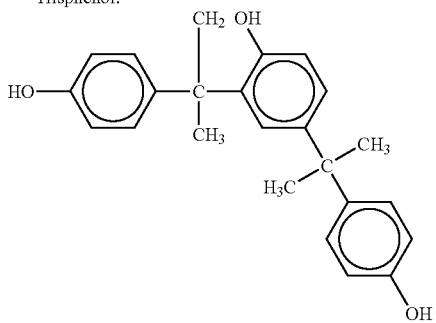

****Hydroxy Cumyl Codimers:

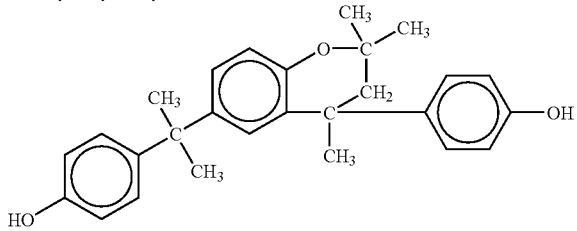

Sulfur Species Analysis

The presence of sulfur by-products in the MeSH and the BMTP promoted reactions were measured by GC-MS of the reaction mixtures. Analysis showed the presence of three sulfur species in each case: methyl mercaptan (MeSH), BMTP and 4-thiomethyl-4-methyl-2-pentanone (TMP). The relative concentrations of the three sulfur species were virtually the same in both the MeSH and BMTP promoted reactions. This is consistent with rapid equilibration of BMTP and MeSH leading to the same distribution of sulfur species under reaction conditions. The small amount of dimethyl disulfide found in the MeSH-promoted reaction was shown to be impurity in MeSH. All numbers were relative areas.

| Promoter | % Acetone conversion | MeSH | BMTP | TMP | Dimethyl Disulfide |
|---|---|---|---|---|---|
| MeSH | 90 | 32.2 | 54.6 | 11.7 | 1.5 |
| BMTP | 90 | 37.8 | 51.8 | 10.4 | 0 |

EXAMPLE 2

This example shows the degree of dissociation of BMTP in mixtures with phenol, acetone, water and phenolic mother liquor as shown in the table below.

| | | Sample No. | | | | |
|---|---|---|---|---|---|---|
| | | 1 Neat BMTP | 2 BMTP & Phenol | 3 CR Feed (Phenol) | 4 CR Feed (ML) | 5 CR Product |
| BMTP | % of total S | 98.9 | 97.8 | 96.2 | 86.9 | 7.2 |
| Water | % wt | — | — | 0.08 | 0.34 | 1.75 |

Sample 1 is undiluted BMTP used as catalyst promoter. Sample 2 is a mixture of BMTP and commercial-grade phenol. Sample 3 is a mixture of BMTP, commercial-grade phenol and LC-grade acetone prepared as condensation reactor CR feed. Sample 4 is a mixture of BMTP, commercial-grade phenol, LC-grade acetone and mother liquor recycle stream from BPA purification. Sample 5 is the condensation reactor effluent stream (Stream 3) using Sample 4 as the feed stream. All samples are analyzed using gas chromatography with a sulfur-specific detector. The percentage of total peak area represented by the BMTP peak is shown for each sample. The water concentration for Samples 3 through 5 is determined by GC/TCD.

EXAMPLE 3

This example shows start up of the reaction system depicted in FIG. 1 for manufacture of BPA using BMTP as promoter for the acid-catalyzed condensation reaction between phenol and acetone. With carbonyl compound stream 2 containing no flow, liquid phenol is charged into condensation reactor CR containing acidic ion exchange resin with a cation exchange capacity greater than about 4.0 meq/g dry weight through phenolic compound/mother liquor stream 1 and condensation reactor feed stream 126, and through first phenolic compound stream 5 into the promoter absorber column PC. The temperature of the contents of condensation reactor CR is brought up to about 60° C. Phenol flows from the condensation reactor CR to the dehydration column DC via condensation reactor effluent stream 3 and leaves the dehydration column DC from the dehydration column bottoms stream 8 and dehydration column overhead stream 4. Phenol flow is also established from the bottom of the promoter absorber column PC into the promoter absorber column bottoms stream 6 and in second phenolic compound stream 9. Water is introduced into the condensation reactor CR via stream 126 by adding it to streams 1, 2 and/or 6 to create a water level of about 0.75 wt % of the condensation reactor CR inventory (about 3.75 mol %). BMTP is then introduced into the system at injection point A until the methyl mercaptan level in the condensation reactor CR reaches about 0.5 wt % (0.95 mol %). Water is maintained in excess during this procedure by the rate of BMTP injection into point A being controlled to insure that water is in molar excess to methyl mercaptan. For example, the water/methyl mercaptan molar ratio in the condensation reactor is maintained at greater than about 1.0, preferably greater than about 2.0. The total BMTP introduced into the system is such that it would be equivalent to about 0.5 wt % (0.95 mol %) of the condensation reactor CR inventory. Point A is contained within the recirculation loop created by the vapor recirculation stream 11 from the promoter absorber column PC and the point at which it intersects the dehydration column overhead stream 4, upstream of pump P1. It is noted that BMTP is not injected into a nearly stagnant stream during startup.

EXAMPLE 4

Into the reaction system started up as in Example 3, liquid acetone is fed into carbonyl stream 2 to achieve the material balance at BPA manufacturing operation as follows: Liquid condensation reactor effluent stream 3 comprises about 540 parts phenol, 257 parts BPA, 18 parts water, 5 parts acetone, 9 parts methyl mercaptan and 90 parts other species. The vapor dehydration column overhead stream 4 comprises about 5 parts acetone, 1 part water and 9 parts methyl mercaptan, and the liquid dehydration column bottoms stream 8 comprises about 257 parts BPA and 538 parts phenol. The liquid promoter absorber column bottoms stream 6 comprises about 249 parts phenol, 5 parts acetone, 9 parts methyl mercaptan and 1 part water.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What we claim is:

1. A process reaction system for manufacturing polyphenol at polyphenol manufacturing conditions comprising a phenolic compound/mother liquor stream, a carbonyl compound stream, a condensation reactor comprising an acid catalyst and maintained under polyphenol manufacturing conditions, a condensation reactor effluent stream to a dehydration column, a dehydration column, a dehydration column overhead stream under vacuum created by a downstream first pump to a promoter absorber column, a dehydration column side draw stream, a dehydration column bottoms stream, a promoter absorber column, a vent stream from the promoter absorber column, a vapor recirculation stream from the promoter absorber column to the dehydration column overhead stream upstream of the first pump, a promoter absorber column bottoms stream, a first phenolic compound stream, a second phenolic compound stream to the liquid ring inlet port of the first pump and a condensation reactor feed stream comprising the phenolic compound/mother liquor stream, the carbonyl compound stream and the promoter absorber column bottoms stream to the condensation reactor comprising an acid catalyst, said process reaction system comprising a phenolic compound reactant, a carbonyl compound reactant and bismethylthiopropane catalyst promoter composition, said bismethylthiopropane catalyst promoter composition being added to said process reaction system in at least one of (a) the dehydration column overhead stream downstream of the dehydration column, downstream of the point at which the vapor recirculation stream intersects the dehydration column overhead stream and upstream of the first pump creating a vacuum in said dehydration column overhead stream, (aa) the dehydration column overhead stream downstream of the dehydration column, upstream of the point at which the vapor recirculation stream intersects the dehydration column overhead stream and upstream of the first pump creating a vacuum in said dehydration column overhead stream, (b) the second phenolic compound stream to the liquid ring inlet port of the first pump creating a vacuum on said dehydration column, (c) the promoter absorber column, (d) the carbonyl compound stream upstream of the junction with the promoter absorber column bottoms stream, (e) the promoter absorber column bottoms stream upstream of the junction with the carbonyl compound stream or (f) the phenolic compound/mother liquor stream.

2. The process system of claim 1, wherein the phenolic compound comprises phenol, and the carbonyl compound comprises acetone.

3. The process system of claim 1, wherein the acid catalyst comprises an acidic cation exchange resin having a cation exchange capacity of greater than 4.0 meq/g dry weight.

4. The process system of claim 1, wherein the polyphenol manufacturing conditions include a temperature of from about 20° C. to about 130° C. and a contact time of the polyphenol and carbonyl compounds over the acid catalyst equivalent to a weight hourly space velocity of from about 0.1 to about 10 hr$^{-1}$.

5. The process system of claim 1, wherein said polyphenol product comprises bisphenol-A.

6. The process system of claim 1, wherein said catalyst promoter composition is added to said process reaction system in at least one of (a) the dehydration column overhead stream downstream of the dehydration column, downstream of the point at which the vapor recirculation stream intersects the dehydration column overhead stream and upstream of the first pump creating a vacuum in said dehydration column overhead stream, (aa) the dehydration column overhead stream downstream of the dehydration column, upstream of the point at which the vapor recirculation stream intersects the dehydration column overhead stream and upstream of the first pump creating a vacuum in said dehydration column overhead stream, (b) the second phenolic compound stream to the liquid ring inlet port of the first pump creating a vacuum on said dehydration column, (c) the promoter absorber column or (d) the carbonyl compound stream upstream of the junction with the promoter absorber column bottoms stream.

7. The process system of claim 6, wherein said catalyst promoter composition is added to said process reaction system at the dehydration column overhead stream downstream of the dehydration column, downstream of the point at which the vapor recirculation stream intersects the dehydration column overhead stream and upstream of the first pump creating a vacuum in said dehydration column overhead stream.

8. The process system of claim 7, wherein the phenolic compound comprises phenol, and the carbonyl compound comprises acetone.

9. The process system of claim 7, wherein the acid catalyst comprises an acidic cation exchange resin having a cation exchange capacity of greater than 4.0 meq/g dry weight.

10. The process system of claim 7, wherein the polyphenol manufacturing conditions include a temperature of from about 20° C. to about 130° C. and a contact time of the polyphenol and carbonyl compounds over the acid catalyst equivalent to a weight hourly space velocity of from about 0.1 to about 10 hr$^{-1}$.

11. The process system of claim 7, wherein said polyphenol product comprises bisphenol-A.

12. The process system of claim 1, which is started with steps comprising (1) adding liquid phenolic compound into the condensation reactor maintained at a temperature of from about 20° C. to about 130° C. and containing acidic catalyst through the condensation reactor feed stream comprising the contents of the phenolic compound/mother liquor stream and the promoter absorber column bottoms stream, (2) adding phenolic compound into the promoter absorber column, (3) adding water into the promoter absorber column or the condensation reactor feed stream at a rate to create a water level of from about 0.5 wt % to about 2.0 wt % of the condensation reactor inventory, (4) adding bismethylthiopropane into the reaction system at an injection point at a rate to maintain a water/methyl mercaptan molar ratio in the condensation reactor greater than about 1.0 until the methyl mercaptan in the condensation reactor reaches 0.25 wt % to 2.0% wt, whereby the bismethylthiopropane injection point is at least one of (a) in the dehydration column overhead stream downstream of the dehydration column, downstream of the point at which the vapor recirculation stream intersects the dehydration column overhead stream and upstream of the first pump creating a vacuum in said dehydration column overhead stream, (b) in the second phenolic compound stream to the liquid ring inlet port of the first pump creating a vacuum on said dehydration column, (c) in the promoter absorber column or (d) in the carbonyl compound stream upstream of the junction with the promoter absorber column bottoms stream, and whereby the rate of bismethylthiopropane injection is controlled to insure that water is in molar excess to methyl mercaptan in the condensation reactor.

13. The process system of claim 12, wherein the phenolic compound comprises phenol and the bismethylthiopropane is added into the reaction system at an injection point at a rate to maintain the water/methyl mercaptan molar ratio in the condensation reactor greater than about 1.0 until the methyl mercaptan in the condensation reactor reaches 0.5 wt % to 1% wt.

14. The process system of claim 12, wherein the bismethylthiopropane is added to said process reaction system at an injection point in the dehydration column overhead stream downstream of the dehydration column, downstream of the point at which the vapor recirculation stream intersects the dehydration column overhead stream and upstream of the first pump creating a vacuum in said dehydration column overhead stream.

15. The process system of claim 1, wherein the molar ratio of phenolic compound to carbonyl compound in the condensation reactor is at least about 2.

16. The process system of claim 15, wherein the molar ratio of phenolic compound to carbonyl compound in the condensation reactor is from about 4 to about 25.

17. The process system of claim 15, wherein the amount of bismethylthiopropane added to said process reaction system is sufficient to maintain a methyl mercaptan level in the condensation reactor of from about 0.25 to about 2.0 wt %.

18. The process system of claim 2, wherein the molar ratio of phenol to acetone in the condensation reactor is at least about 2.

19. The process system of claim 18, wherein the molar ratio of phenol to acetone in the condensation reactor is from about 4 to about 25.

20. The process system of claim 18, wherein the amount of bismethylthiopropane added to said process reaction system is sufficient to maintain a methyl mercaptan level in the condensation reactor of from about 0.25 to about 2.0 wt %.

21. The process system of claim 6, wherein the molar ratio of phenolic compound to carbonyl compound in the condensation reactor is at least about 2.

22. The process system of claim 21, wherein the molar ratio of phenolic compound to carbonyl compound in the condensation reactor is from about 4 to about 25.

23. The process system of claim 21, wherein the amount of bismethylthiopropane added to said process reaction system is sufficient to maintain a methyl mercaptan level in the condensation reactor of from about 0.25 to about 2.0 wt %.

24. The process system of claim 7, wherein the molar ratio of phenolic compound to carbonyl compound in the condensation reactor is at least about 2.

25. The process system of claim 24, wherein the molar ratio of phenolic compound to carbonyl compound in the condensation reactor is from about 4 to about 25.

26. The process system of claim 24, wherein the amount of bismethylthiopropane added to said process reaction system is sufficient to maintain a methyl mercaptan level in the condensation reactor of from about 0.25 to about 2.0 wt %.

27. The process system of claim 8, wherein the molar ratio of phenol to acetone in the condensation reactor is at least about 2.

28. The process system of claim 27, wherein the molar ratio of phenol to acetone in the condensation reactor is from about 4 to about 25.

29. The process system of claim 27, wherein the amount of bismethylthiopropane added to said process reaction system is sufficient to maintain a methyl mercaptan level in the condensation reactor of from about 0.25 to about 2.0 wt %.

30. In a process for manufacturing a polyphenol compound in the presence of an acid catalyst by adding into a reaction zone containing said acid catalyst and maintained at polyphenol manufacturing conditions a phenolic compound reactant, a carbonyl compound reactant and a catalyst promoter comprising bismethylthiopropane, the improvement comprising adding said catalyst promoter to said process in at least one of (a) a dehydration column overhead stream downstream of the dehydration column, downstream of the point at which a vapor recirculation stream intersects the dehydration column overhead stream and upstream of a first pump creating a vacuum in said dehydration column overhead stream, (aa) a dehydration column overhead stream downstream of a dehydration column, upstream of the point at which a vapor recirculation stream intersects the dehydration column overhead stream and upstream of a first pump creating a vacuum in said dehydration column overhead stream, (b) a second phenolic compound stream to the liquid ring inlet port of a first pump creating a vacuum on a dehydration column, (c) a promoter absorber column, (d) a carbonyl compound stream upstream of the junction with a promoter absorber column bottoms stream, (e) a promoter absorber column bottoms stream upstream of the junction with a carbonyl compound stream or (f) a phenolic compound/mother liquor stream.

31. The process of claim 30, wherein the phenolic compound comprises phenol, and the carbonyl compound comprises acetone.

32. The process of claim 30, wherein the acid catalyst comprises an acidic cation exchange resin having a cation exchange capacity of greater than 4.0 meq/g dry weight.

33. The process of claim 30, wherein the polyphenol manufacturing conditions include a temperature of from about 20° C. to about 130° C. and a contact time of the polyphenol and carbonyl compounds over the acid catalyst equivalent to a weight hourly space velocity of from about 0.1 to about 10 $hr^{-1}$.

34. The process of claim 30, wherein said polyphenol compound comprises bisphenol-A.

35. The process of claim 30, wherein said catalyst promoter is added to said process in at least one of (a) a dehydration column overhead stream downstream of the dehydration column, downstream of the point at which a vapor recirculation stream intersects the dehydration column overhead stream and upstream of a first pump creating a vacuum in said dehydration column overhead stream, (aa) a dehydration column overhead stream downstream of a dehydration column, upstream of the point at which a vapor recirculation stream intersects the dehydration column overhead stream and upstream of a first pump creating a vacuum in said dehydration column overhead stream, (b) a second phenolic compound stream to the liquid ring inlet port of a first pump creating a vacuum on a dehydration column, (c) a promoter absorber column, (d) a carbonyl compound stream upstream of the junction with a promoter absorber column bottoms stream.

36. The process of claim 35, wherein said catalyst promoter composition is added to said process at a dehydration column overhead stream downstream of the dehydration column, downstream of the point at which a vapor recirculation stream intersects the dehydration column overhead stream and upstream of a first pump creating a vacuum in said dehydration column overhead stream.

37. The process of claim 36, wherein the phenolic compound comprises phenol, and the carbonyl compound comprises acetone.

38. The process of claim 36, wherein the acid catalyst comprises an acidic cation exchange resin having a cation exchange capacity of greater than 4.0 meq/g dry weight.

39. The process of claim 36, wherein the polyphenol manufacturing conditions include a temperature of from about 20° C. to about 130° C. and a contact time of the polyphenol and carbonyl compounds over the acid catalyst equivalent to a weight hourly space velocity of from about 0.1 to about 10 $hr^{-1}$.

40. The process system of claim 36, wherein said polyphenol compound comprises bisphenol-A.

* * * * *